(12) United States Patent
Shadduck

(10) Patent No.: US 9,179,965 B2
(45) Date of Patent: Nov. 10, 2015

(54) SUPERCAVITATING MEDICAL PROBE AND METHOD OF USE

(76) Inventor: John H. Shadduck, Berkeley, CA (US)

(*) Notice: Subject to any disclaimer, the term of this patent is extended or adjusted under 35 U.S.C. 154(b) by 2183 days.

(21) Appl. No.: 11/300,689

(22) Filed: Dec. 14, 2005

(65) Prior Publication Data

US 2006/0229598 A1    Oct. 12, 2006

Related U.S. Application Data

(63) Continuation-in-part of application No. 11/065,180, filed on Feb. 23, 2005, now Pat. No. 7,220,261, which is a continuation of application No. 10/282,555, filed on Oct. 28, 2002, now Pat. No. 6,890,332, which is a continuation-in-part of application No. 09/614,163, filed on Jul. 11, 2000, now abandoned, which is a continuation-in-part of application No. 09/317,768, filed on May 24, 1999, now abandoned.

(60) Provisional application No. 60/636,352, filed on Dec. 14, 2004, provisional application No. 60/636,355, filed on Dec. 14, 2004, provisional application No. 60/348,327, filed on Oct. 27, 2001.

(51) Int. Cl.
| | |
|---|---|
| *A61B 18/14* | (2006.01) |
| *A61B 17/22* | (2006.01) |
| *A61B 18/00* | (2006.01) |
| *A61B 18/18* | (2006.01) |
| *A61F 9/007* | (2006.01) |

(52) U.S. Cl.
CPC ..... *A61B 18/148* (2013.01); *A61B 2017/22014* (2013.01); *A61B 2018/00208* (2013.01); *A61B 2018/1861* (2013.01); *A61B 2218/002* (2013.01); *A61B 2218/007* (2013.01); *A61F 9/0079* (2013.01)

(58) Field of Classification Search
CPC .. A61B 18/002; A61B 18/007; A61B 18/148; A61B 2018/00184–2018/00208; A61B 2018/1861; A61B 2017/22014; A61F 9/0079
USPC ............. 606/41, 1, 34, 32, 169, 45, 48–50; 128/898; 600/437, 439, 407
See application file for complete search history.

(56) References Cited

U.S. PATENT DOCUMENTS

| | | | | |
|---|---|---|---|---|
| 4,747,821 | A | * | 5/1988 | Kensey et al. ............... 604/22 |
| 5,281,217 | A | | 1/1994 | Edwards et al. |
| 5,873,855 | A | | 2/1999 | Eggers et al. |
| 5,888,198 | A | | 3/1999 | Eggers et al. |
| 5,891,095 | A | | 4/1999 | Eggers et al. |

(Continued)

OTHER PUBLICATIONS

U.S. Appl. No. 09/566,768, filed May 8, 2000, in the name of Shadduck, Non-Final Rejection mailed Jan. 16, 2002.

(Continued)

*Primary Examiner* — Michael Peffley
*Assistant Examiner* — Samantha Good
(74) *Attorney, Agent, or Firm* — Levine Bagade Han LLP

(57) ABSTRACT

An electrosurgical working end that utilizes supercavitation phenomenon for controlled application of electrosurgical energy to tissue. In one preferred method of the invention, the system utilizes an electrosurgical surface that is rotatable in a liquid substance at very high surface velocities capable of localized lowering of the pressure of the substance below its saturated vapor pressure to cause supercavitation, and contemporaneously applying electrical energy from the electrosurgical surface across the cavity to ablate adjacent tissue. The system creates supercavitation with surface velocities of greater than about 70 m/sec in a liquid substance by means of high speed rotation and optionally ultrasound actuation.

13 Claims, 11 Drawing Sheets

(56) References Cited

U.S. PATENT DOCUMENTS

| | | | |
|---|---|---|---|
| 5,989,248 | A | 11/1999 | Tu et al. |
| 6,024,733 | A | 2/2000 | Eggers et al. |
| 6,032,674 | A | 3/2000 | Eggers et al. |
| 6,066,134 | A | 5/2000 | Eggers et al. |
| 6,394,956 | B1 | 5/2002 | Chandrasekaran et al. |
| 6,890,332 | B2 | 5/2005 | Truckai et al. |
| 7,220,261 | B2 | 5/2007 | Truckai et al. |
| 2003/0009166 | A1* | 1/2003 | Moutafis et al. ............... 606/49 |
| 2003/0125727 | A1* | 7/2003 | Truckai et al. ................ 606/41 |
| 2004/0193095 | A1 | 9/2004 | Shadduck et al. |
| 2006/0058782 | A1 | 3/2006 | Truckai et al. |
| 2007/0213704 | A1 | 9/2007 | Truckai et al. |

OTHER PUBLICATIONS

U.S. Appl. No. 09/614,163, filed Jul. 11, 2000, in the name of Shadduck, Non-Final Rejection mailed Jun. 20, 2002.

U.S. Appl. No. 09/9317,768, filed May 24, 1999, in the name of Shadduck, Final Rejection mailed May 23, 2001.

U.S. Appl. No. 09/9317,768, filed May 24, 1999, in the name of Shadduck, Non-Final Rejection mailed Oct. 5, 2000.

U.S. Appl. No. 10/282,555, filed Oct. 28, 2002, in the name of Truckai, Non-Final Rejection mailed Jun. 16, 2004.

U.S. Appl. No. 10/282,555, filed Oct. 26, 2002, in the name of Truckai, Notice of Allowance mailed Nov. 15, 2004.

U.S. Appl. No. 11/065,180, filed Feb. 23, 2005, in the name of Truckai, Non-Final Rejection mailed Jun. 30, 2006.

U.S. Appl. No. 11/065,180, filed Feb. 23, 2005, in the name of Truckai, Notice of Allowance mailed Jan. 18, 2007.

U.S. Appl. No. 11/735,318, filed Apr. 13, 2007, in the name of Truckai, Final Rejection mailed Jul. 7, 2009.

U.S. Appl. No. 11/735,318, filed Apr. 13, 2007, in the name of Truckai, Non-Final Rejection mailed Nov. 12, 2008.

* cited by examiner

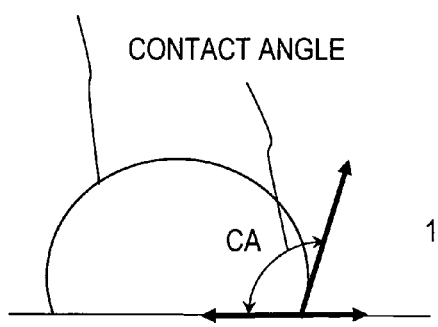
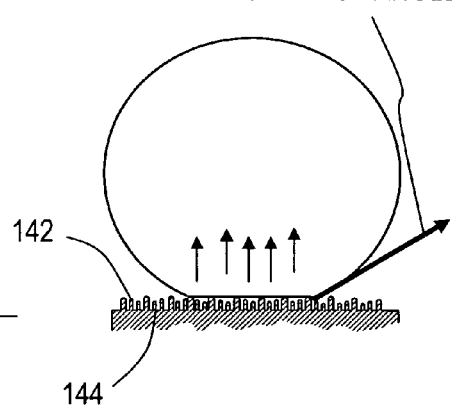
FIG. 3B
FIG. 3C

SUPERCAVITATING MEDICAL PROBE AND METHOD OF USE

CROSS-REFERENCE TO RELATED APPLICATIONS

This application claims benefit of Provisional U.S. Patent Application Ser. No. 60/636,352 filed Dec. 14, 2004 titled Supercavitating Electrosurgical Device and Method of Use, and also claims benefit of Provisional U.S. Patent Application Ser. No. 60/636,355 filed Dec. 14, 2004 titled Supercavitating Medical Probe and Method of Use, both of which are incorporated herein and made a part of the specification. This application is also a continuation-in-part of U.S. patent application Ser. No. 11/065,180, filed Feb. 23, 2005 now U.S. Pat. No. 7,220,261, titled Electrical Discharge Devices and Techniques for Medical Procedures which is a continuation of U.S. patent application Ser. No. 10/282,555, filed Oct. 28, 2002 now U.S. Pat. No. 6,890,332 titled Electrical Discharge Devices and Techniques for Medical Procedures which claims benefit of Provisional U.S. Patent Application Ser. No. 60/348,327 filed Oct. 27, 2001. U.S. patent application Ser. No. 10/282,555 is also a continuation-in-part of U.S. patent application Ser. No. 09/614,163 filed Jul. 11, 2000, now abandoned which is a continuation-in-part of U.S. patent application Ser. No. 09/317,768 filed May 24, 1999, now abandoned.

BACKGROUND OF THE INVENTION

1. Field of the Invention

The invention is related to instruments and techniques for controlled application of energy to tissue, and more particularly relates to supercavitating surfaces and electrosurgical surfaces for ablating tissue layers, for ablating holes in soft tissue and for ablating occlusive materials, calculi and the like.

2. Description of the Related Art

Various electromagnetic and acoustic energy delivery sources have been investigated for surgical tissue ablation or removal, including radiofrequency (Rf) energy delivery, high intensity focused ultrasound (HIFU) tissue interactions and microwave energy absorption in tissue. In general, at high intensities, the above listed energy sources generate thermal effects that can vaporize tissue as the means of tissue ablation or removal. In other words, the energy sources elevate the temperature of water in intra- and extracellular spaces to above 100° C. thereby explosively vaporizing water to damage or destroy the tissue. The drawback to such purely thermally-mediated ablations is significant collateral damage to tissue volumes adjacent to the targeted site. While in many surgical fields the above-described collateral thermal damage may be acceptable, in fields in which thin layer ablations are required such as ophthalmology, neurology and interventional cardiology, there is a need to prevent, or limit, any such collateral damage.

Radiofrequency currents in tissue have been known for many years in the prior art for cutting a tissue mass or for coagulating regions within a tissue mass. Conventional electrosurgical systems known in the art ablate tissue by applying an electrical field across the targeted tissue. The actual energy-tissue interaction in Rf cutting is typically described in terms of a voltage differential that first boils a fluid and then causes a spark or arc across a vapor gap between an active electrode and the targeted site (e.g., coupled to a return electrode). Conventional electrosurgical ablation is generally achieved at frequencies ranging from 500 kHz to 2.5 MHz, with power levels ranging from 75 to 750 W. In such prior art tissue cutting with Rf currents, the current density rapidly decreases with distance from the exact energy deposition site on the tissue which is contacted by the spark. Still, the depth of tissue disruption and damage in such prior art electrosurgical cutting may range from about 0.3 mm. to as much as 3.5 mm. (see R. D. Tucker et al, *Histologic characteristics of electrosurgical injuries, Journal Am. Assoc. Gynecol. Laparoscopy* 4(2), pp. 201-206 1997.) The depth of tissue ablation depends on several variables, including (i) the conductivity of the tissue, (ii) the insulative characteristics of the media in the physical gap between the active electrode(s) and the tissue; (iii) the dimension of the physical gap between the electrode(s) and the tissue; (iv) the power setting and optional feedback control of the power level based upon electrical characteristics of the targeted tissue; (v) and the translation of the working end relative to the tissue.

One prior art system in the field of electrosurgical ablation was invented by Eggers et al and is described as a Coblator™ (see. e.g., disclosures of Eggers et al in U.S. Pat. Nos. 5,873,855; 5,888,198; 5,891,095; 6,024,733; 6,032,674; 6,066,134 and the companion patents cited therein). The Coblator™ system relies on the creation of a voltage difference between a plurality of closely spaced rod-like electrode elements in a distal working end and a return electrode on the instrument shaft. The Coblator™ system introduces an electrically conductive fluid such as isotonic saline into the physical gaps about a group of closely spaced active electrodes, and between the electrode group and the targeted tissue. The system applies electrical energy with a frequency of about 100 kHz and a voltage of about 100 to 300 V. The Coblator™ promotional materials explain that at high voltage levels, the electrically conductive fluid in the gaps between the closely spaced active electrodes is converted to steam and then into a plasma. The supposition underlying the Coblator™ is that the actual energy-tissue interaction produced by the system relates to charged particles in the plasma having sufficient energy to cause dissociation of molecular bonds within tissue structures that come into contact with the plasma. Based on this hypothesis, the accelerated charged particles have a very short range of travel, and the energy-tissue interaction causes molecular dissociation of tissue surfaces in contact with the plasma.

The types of ablation caused by conventional electrosurgical ablation and the ablation caused by the Coblator™ system share several common characteristics. While conventional ablations and the Coblator™ ablations are suitable for many procedures, both types of ablation are caused by intense energy delivery that boils a fluid (or water in tissue) to create an insulative steam layer which then is energized into a plasma in an interface with tissue.

SUMMARY OF THE INVENTION

Cavitation is a phenomenon known to engineers in the field of fluid dynamics wherein small cavities of a partial vacuum form in a liquid substance wherein the cavities then rapidly collapse. In one example, cavitation occurs when water is forced to move at extremely high speed, e.g., in fluid flows around an obstacle such as a rapidly spinning propeller. In such an example, the pressure of the fluid drops due to its high speed flows (Bernoulli's principle). When the pressure drops below its saturated vapor pressure, its create a plurality of cavities in the water-hence the term cavitation. The cavities can take on a number or forms and configurations that all consist of regions or bubbles of a partial vacuum, i.e., very low pressure gas phase water.

In conventional hydrodynamic terms, cavitation is an unintended and undesirable phenomenon. The regions of cavitation are transient as the cavities implode when the fluid flow velocities subside resulting in a sudden rise in ambient pressure. The collapse of the cavities can cause very strong local shockwaves in the fluid, which may be audible and may damage adjacent structures.

Supercavitation is a related phenomenon in which a partial vacuum envelope is created by high speed fluid flows in a much larger and sustained manner than conventional cavitation to create a supercavity. A supercavitating object's main features are a surface forms for inducing such cavitation—which often include flat surfaces and sharp, streamlined and aqua- or aerodynamic edges which are believed to induce cavitation. When such surface features interact by traveling through, or rotating in, a fluid at surface velocities in the range of 70 m/sec and higher, the liquid is displaced and thereby forced to move around the surface forms with such speeds that it creates an envelope of a partial vacuum. At suitable surface velocities, a sustainable supercavity can be formed. As used herein, the term supercavity is used to describe a cavity that can be sustained at least partially about a moving and/or oscillating working end surface of a medical probe.

In one example, the supercavitation phenomenon is used to allow objects to travel under water at high speed. The Russian Shkval torpedoes may be the only publicly known practical application of supercavitation technology. The supercavitating Shkval torpedo is believed to rotate at high speed and more importantly has a rocket-powered high straight line velocity. The torpedo body reportedly has faceted cavitators on its nose to induce a cavitation envelope that will extend to cover the entire body when it reaches speeds in excess of about 150-200 km/h under water. Thereafter, the torpedo is no longer moving through water, but through a supercavity akin to air. The sustainable envelope or supercavity results in water wetting very little of the body's surface, thereby drastically reducing viscous drag. The drag reduction reportedly allows for torpedo speeds in excess of 500 km/h.

The present invention utilizes the supercavitation phenomenon in a novel manner relating to application of electrosurgical energy to tissue. In accordance with a method of the invention, the system utilizes an electrosurgical surface that is rotatable by a motor drive and/or actuatable by ultrasound in a liquid substance to create and confine a non-equilibrium supercavity proximate to, or in contact with, a site on body structure targeted for ablation. The system includes means for applying high frequency voltage to and across the supercavity which results in arcs of electrical energy across the supercavitation envelope to thereby ablate the targeted site.

The present invention differs greatly from the prior art means described above for delivering ablative electrical energy to tissue. The invention provides a supercavity of a partial vacuum that is cold, and does not have a thermal energy delivery component as in conventional Rf ablation or the Coblator™ system that thermally vaporizes saline and then applies further energy to create an energetic plasma.

The invention provides a supercavitating electrode for ablation of biological material. The invention provides a method for biological material removal that applies voltage about a supercavity induced by high velocity movement of an electrosurgical surface.

These and other objects and advantages of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 3B is an illustration of a fluid droplet on a non-ultrahydrophobic surface.

FIG. 3C is a schematic illustration of an ultrahydrophobic surface of device of FIG. 3A showing a very high contact angle.

DETAILED DESCRIPTION OF THE INVENTION

Figure 1:
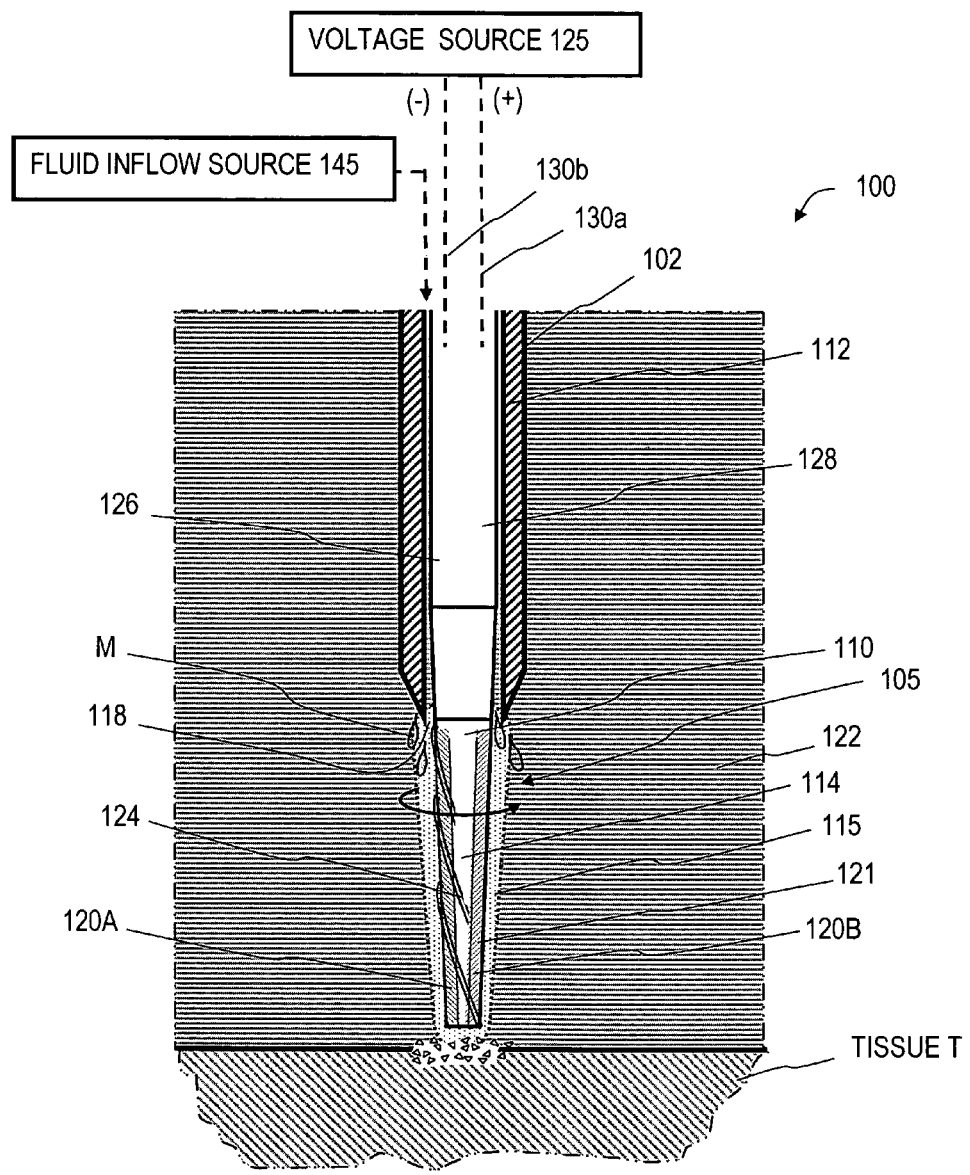
FIG. 1 is a cut-away view of a working end of an exemplary probe of the invention illustrating an electrosurgical working surface with supercavitation occurring about the working surface for enabling application of electrosurgical energy across the cavity to tissue in close proximity to the cavity.

FIG. 1 illustrates an instrument system that comprises a medical probe 100 with a distal portion shown in FIG. 1 that is configured for creating cavitation and supercavitation about an actuatable or moveable surface for controlling the application of electrosurgical energy to tissue. In FIG. 1, an elongated shaft or sleeve member 102 carries an actuatable, moveable working end indicated at 105. In the embodiment of FIG. 1, the actuatable working end 105 comprises an elongated rotatable member 110 that extends through bore 112 in the shaft member 102 and is operatively coupled to a motor drive described further below. The rotatable member 110 and working end 105 is rotatable at a very high speed wherein the working surface 114 creates a cavity or supercavity 115 that can substantially envelope the working end. In the embodiment of FIG. 1, it can be seen that the actuatable working end 105 is exposed to extend outwardly from open termination 118 of bore 112, but the working end 105 can also be partly exposed in a side port of shaft member 102 or can be recessed in an end port of the shaft member 102. The cross section of rotatable member 110 and working end 105 can range between about 0.05 mm and 5.0 mm. In any embodiment, the working surface 114 or electrosurgical surface 121 can have a shape that is rounded, blunt-tipped, tubular, sharp-tipped or bulbous-tipped.

The embodiment of FIG. 1 has an actuatable, rotatable working end 105 that carries at least one electrode. More particularly, the working end 105 of FIG. 1 comprises an electrosurgical energy delivery surface that includes first polarity electrode 120A and second opposing polarity electrode 120B for operating in a bi-polar manner. The term bi-polar as used herein connotes that both polarity electrode surfaces are in close proximity in the working end of the instrument. In another embodiment, the working end can carry a first polarity electrode 120A and the second polarity electrode can be located in shaft portion 102 or the second polarity electrode can comprise a ground pad to operate in a mono-polar manner as is known in the art. In a typical embodiment of the invention, the actuatable working end 105 is configured for causing cavitation and includes at least one electrode and is herein also termed an electrosurgical surface 121. Such as electrosurgical surface 121 is operatively connected to a high frequency voltage source and controller indicated at 125. The proximal portion 126 of the rotatable member 110 has an exterior insulator layer 128. In the embodiment of FIG. 1, the voltage source 125 is connected to first and second insulated leads 130a and 130b that extend through the interior of member 110 to respective electrodes 120A and 120B. The coupling of electrical current to a rotating member is accomplished by concentric rotating sleeve connectors in a handle portion of the instrument as in known in the art.

In operation as depicted in FIG. 1, the working end 105 is immersed in a liquid substance 122 such as water, saline or blood. The liquid substance 122 is incompressible and rotation of the working end 105 in the substance at a selected velocity is capable of causing microflows about working surface 114 and cavitation features 124 therein (further described below) to cause localized reduction of the pressure of the substance 122 below its saturated vapor pressure to thereby create a cavity 115 in the substance about the working surface 114. In order to create a cavity 115 that partially or completely surrounds the working surface 114, the surface 114 together with surface cavitation features 124 are configured to achieve a relative surface speed in the liquid substance that exceeds about 70 m/sec. In one embodiment, the rotation drive mechanism coupled to member 110 comprises an air turbine motor or an electric motor known in the art. In one embodiment, an air motor of the type used in dental instruments is used for the invention that can rotate at 100,000 rpm, 200,000 rpm or as high as 400,000 rpm to create a supercavity. The diameter of the rotatable element 110 can range from about 50 microns to about 5 mm and can achieve the surface speeds required to cause cavitation.

Figure 2A:
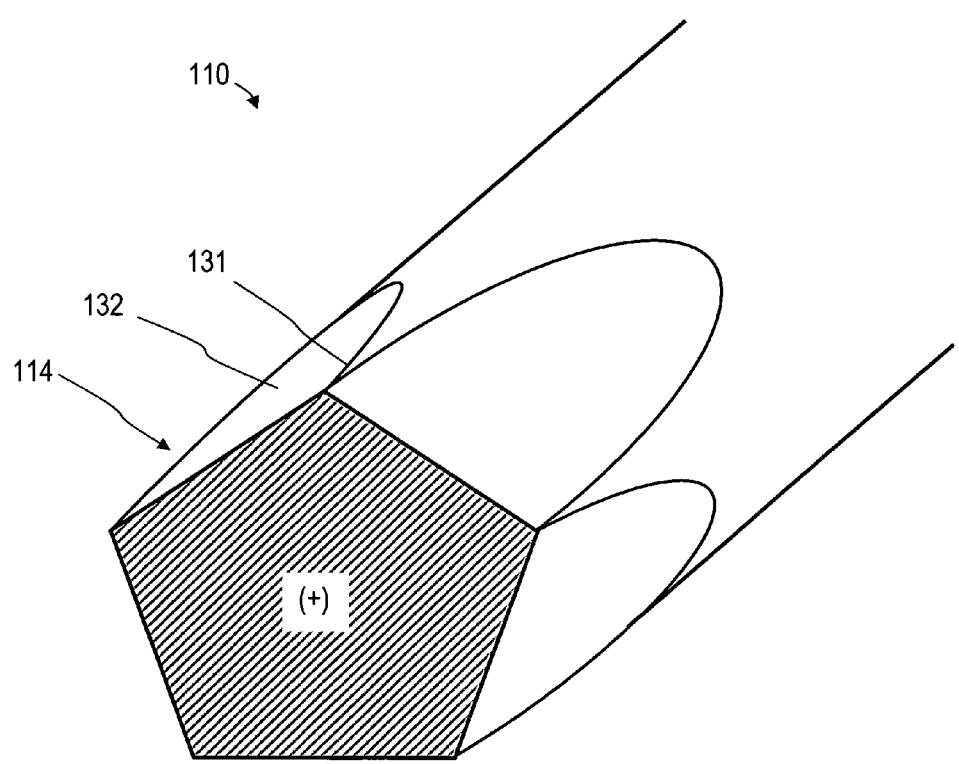
FIG. 2A is a sectional view of an actuatable, rotatable member with surface features for enabling supercavitation about the surface of the actuatable member.
Figure 2B:
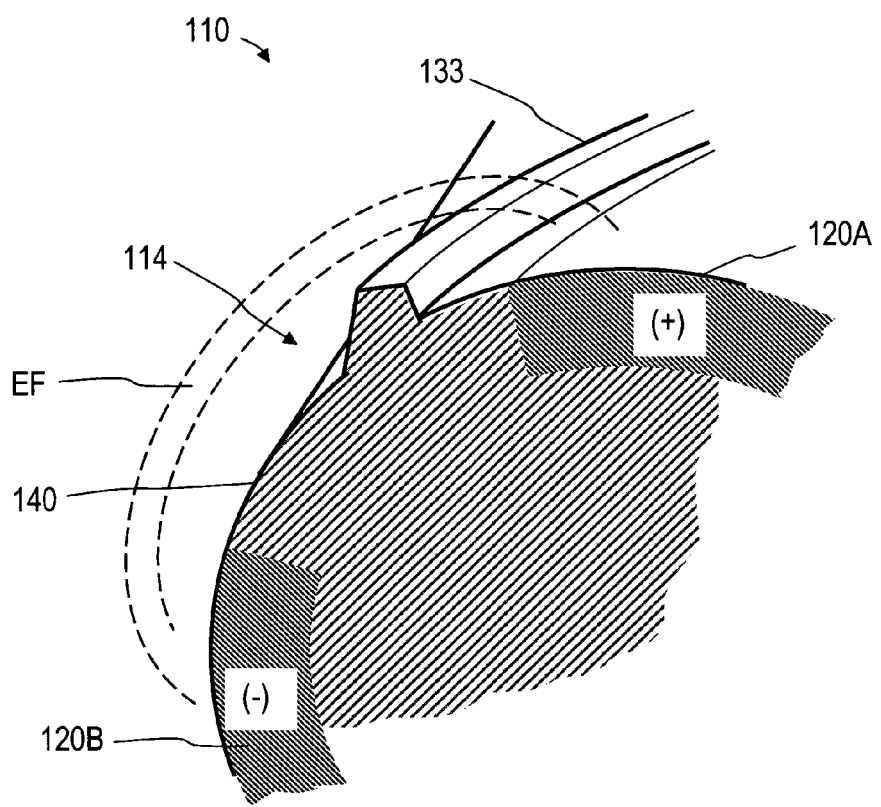
FIG. 2B is a sectional view of a portion of a rotatable member similar to FIG. 2A with alternative surface features.

FIGS. 2A-2D illustrate exemplary features 124 for creating a cavity or supercavity about a working surface 114 or electrosurgical surface 121, wherein the cavitation-inducing surface features comprise non-smooth surfaces. For example, FIG. 2A illustrates a rotatable member 110 that transitions from a smooth surface into a working surface 114 including flattened facets 131 with edges 132 that can induce partial cavitation and supercavitation. The rotatable member 110 is indicated as having a positive polarity for cooperating with a negative polarity electrode located elsewhere in the working end or in a ground pad. In FIG. 2B, the rotatable member 110 carries a plurality of microblades or protrusions 133 that can be any pitch (spiral lead) similar to that suggested in FIG. 1. The member 110 carries spaced apart conductive coatings that comprise opposing polarity electrodes 120A and 120B.

Figure 2C:
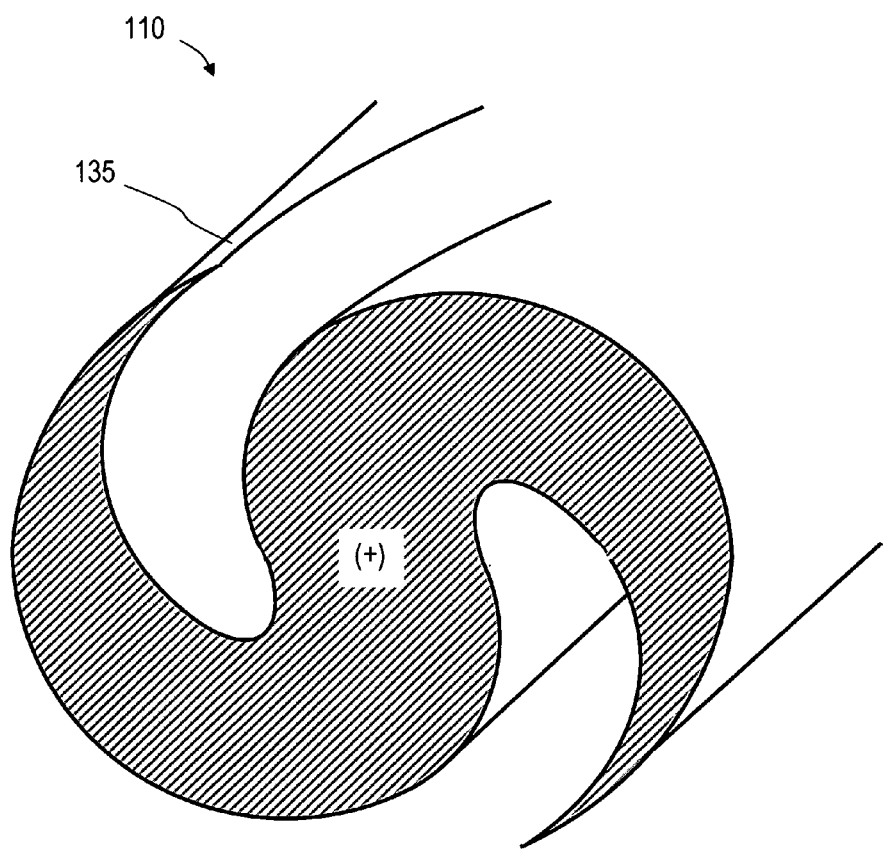
FIG. 2C is a sectional view of a portion of a rotatable member similar to FIGS. 2A-2B with alternative surface features.
Figure 2D:
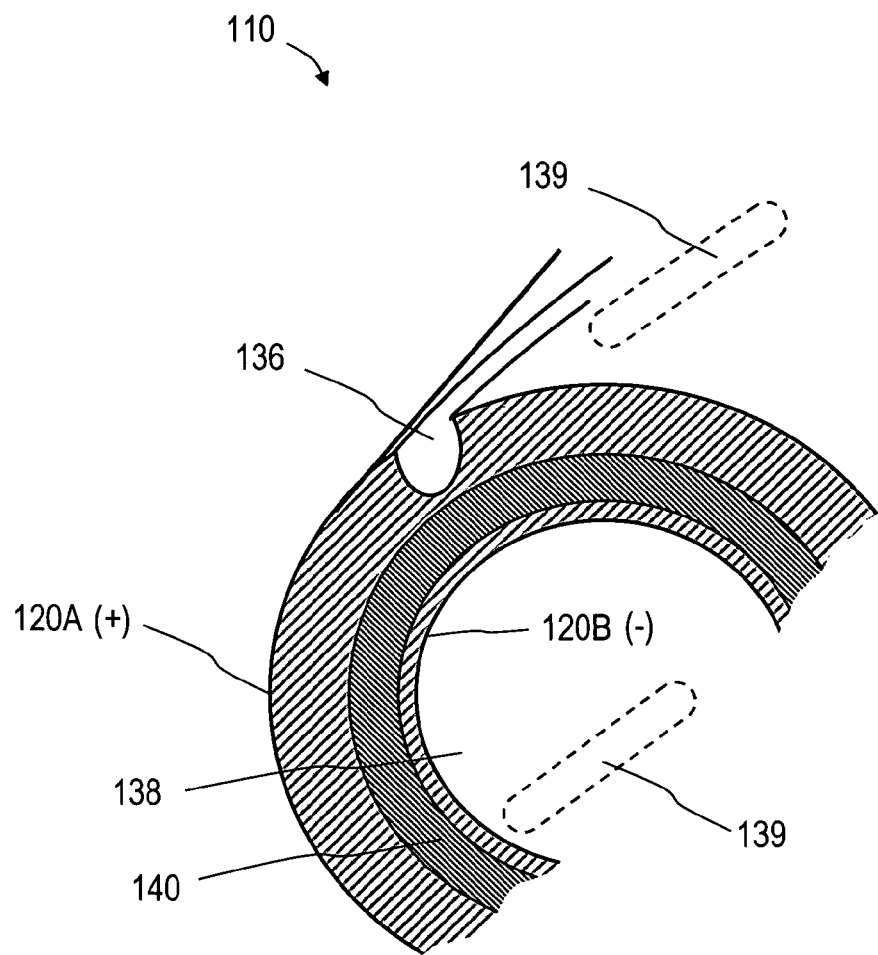
FIG. 2D is a sectional view of a portion of a rotatable member similar to FIGS. 2A-2C with alternative surface features.

FIG. 2B illustrates the electrical field EF or configuration of current flow that can be created about surface 114. In FIG. 2C, the rotatable member 110 carries blades 135 that extend in a suitable arcuate shape and form. FIG. 2D illustrates a tubular spinnable element 110 with grooves 136 and interior bore 138 that also can extend to vents 139 in the surface 114. In the embodiment of FIG. 2D, concentric interior and exterior layers comprise opposing polarity electrodes 120A and 120B with insulator layer 140 therebetween. All of the above geometries it is believed can be configured for causing supercavitation in a liquid substance 122 about a working surface 114 at a selected surface rotation speed in the range of 70 m/sec and higher, and in some cases in the range of 10 m/sec and higher.

Figure 3A:
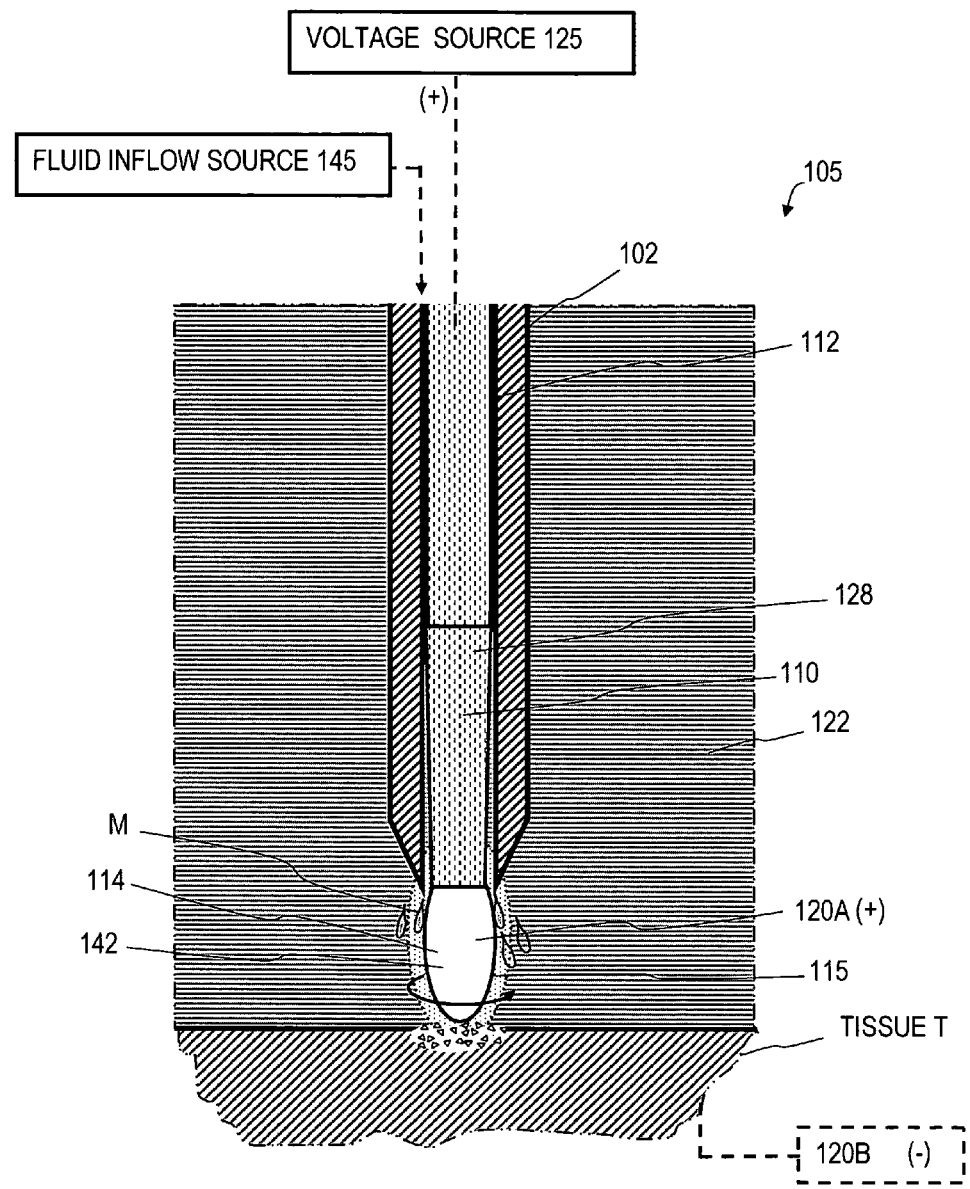
FIG. 3A is a cut-away view of a working end having a rotatable member with ultrahydrophobic surfaces.

In another embodiment, FIG. 3A illustrates an electrosurgical electrode having ultrahydrophobic surface features which it is believed will assist in creating supercavitation about an actuatable or moveable surface 114. As depicted in FIG. 3B, an ultrahydrophobic electrode surface indicated at 142 is profiled with microscopic structures 144 having nearly vertical side walls, wherein an aqueous fluid becomes supported by the tips of the structures 144 due to negative capillary effect. FIG. 3B illustrates a water droplet having a very high contact angle and low sliding resistance (small contact angle hysteresis) on such a surface. For example, the contact angle is above about 105°. In small cross section rotatable members 110, it is believed that the ultrahydrophobic surfaces will reduce drag by a significant amount thus resulting in a thin cavity about the surface. The surface also functions as an electrosurgical surface. The invention encompasses a supercavitating electrosurgical surface wherein the surface has features that assist in developing a supercavity under high speed rotation or oscillation (or both) in a liquid substance 122. The invention further also encompasses any ultrahydrophobic surface electrode whether in a non-cavitating or supercavitating electrosurgical surface.

As can be seen in FIGS. 1 and 3A, the system optionally includes a fluid source 145 that allows inflows of a fluid media M into an interface with targeted tissue, for example through bore 112 or another fluid channel in rotatable member 110. FIG. 2B further illustrates an electrical field EF between the first and second electrodes carried by the rotatable element 110. In FIG. 2B, it can be seen that the electrosurgical surface 121 carries first and second electrodes 120A and 120B in spaced apart axial electrode surfaces with insulator portion 140 therebetween. In an alternative embodiment (not shown), the first and second electrodes 120A and 120B can be configured in an axially spaced apart arrangement on rotatable element 110. In such embodiments, the cross-section ranging of element 110 can range from about 100 microns to about 5 mm. The invention encompasses any mono-polar or bipolar arrangement of first and second opposing polarity electrodes 120A and 120B, or a plurality spaced apart opposing polarity electrodes 120A and 120B in any axial, helical or angular arrangement.

Figure 4:
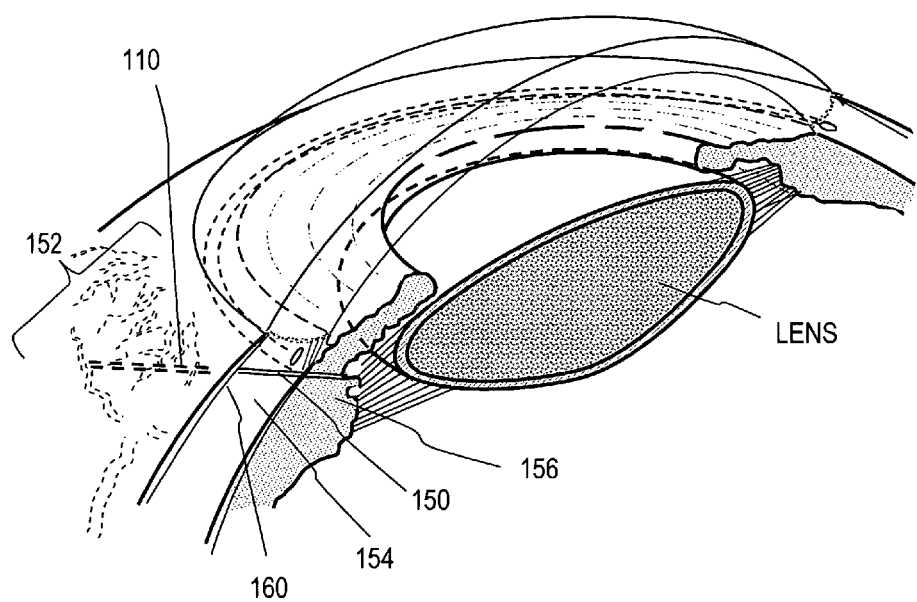
FIG. 4 is a view of a method of practicing the principles of the invention in ablating a bore in ocular tissue to treat ocular hypertension or glaucoma.

In FIG. 4, the method of the invention is depicted schematically in ablating a bore 150 in ocular tissue between a region carrying the eye's lymphatic network 152 through the sclera 154 to a selected region of the ciliary body 156. The creation of a bore 150 can be effective in treating ocular hypertension, using outflows through the lymphatic network in a subconjunctival region 160 as generally described in the author's co-pending U.S. patent application Ser. No. 10/759,797 filed Jan. 17, 2004 which is incorporated herein by this reference. In treating ocular hypertension, the bore 150 in tissue, or a plurality of bores, preferably has a diameter ranging from about 50 microns to 250 microns. Thus, the cross section of the rotatable member 110 as in FIG. 1 can be in this range.

The method of the invention thus comprises: (a) causing a selected rate of relative motion between a liquid substance 122 and a working surface or electrosurgical surface to create a partial cavity or a supercavity, and (b) applying electrical energy across the cavity in close proximity to mammalian body structure to apply ablative energy to the body structure. The method includes translating the electrosurgical surface to ablate a surface region of body structure, or axially moving the electrosurgical surface to ablate a hole in the body structure. In various embodiments, the apparatus of the invention is configured with a working end capable of creating a supercavity around at least a portion of an electrosurgical surface. In another embodiment, the working end creates a cavity that surrounds both first and second polarity electrodes. The method of the invention includes immersing an actuatable working surface in a liquid substance, providing a rate of motion in the working surface capable of localized lowering of the pressure of the substance below the saturated vapor pressure to create a cavity therein, and contemporaneously delivering electrical energy across the cavity to tissue. The method of the invention includes immersing an actuatable working surface in a liquid substance, providing a rate of motion in an immersed working surface that causes localized increase of the impedance of the substance by a factor of at least one hundred, or at least one thousand. The increase in impedance results from the cavity or vaporous form of the low pressure media which in turn results in an insulative gap that electrical energy arcs across to apply energy to tissue.

Figure 5:
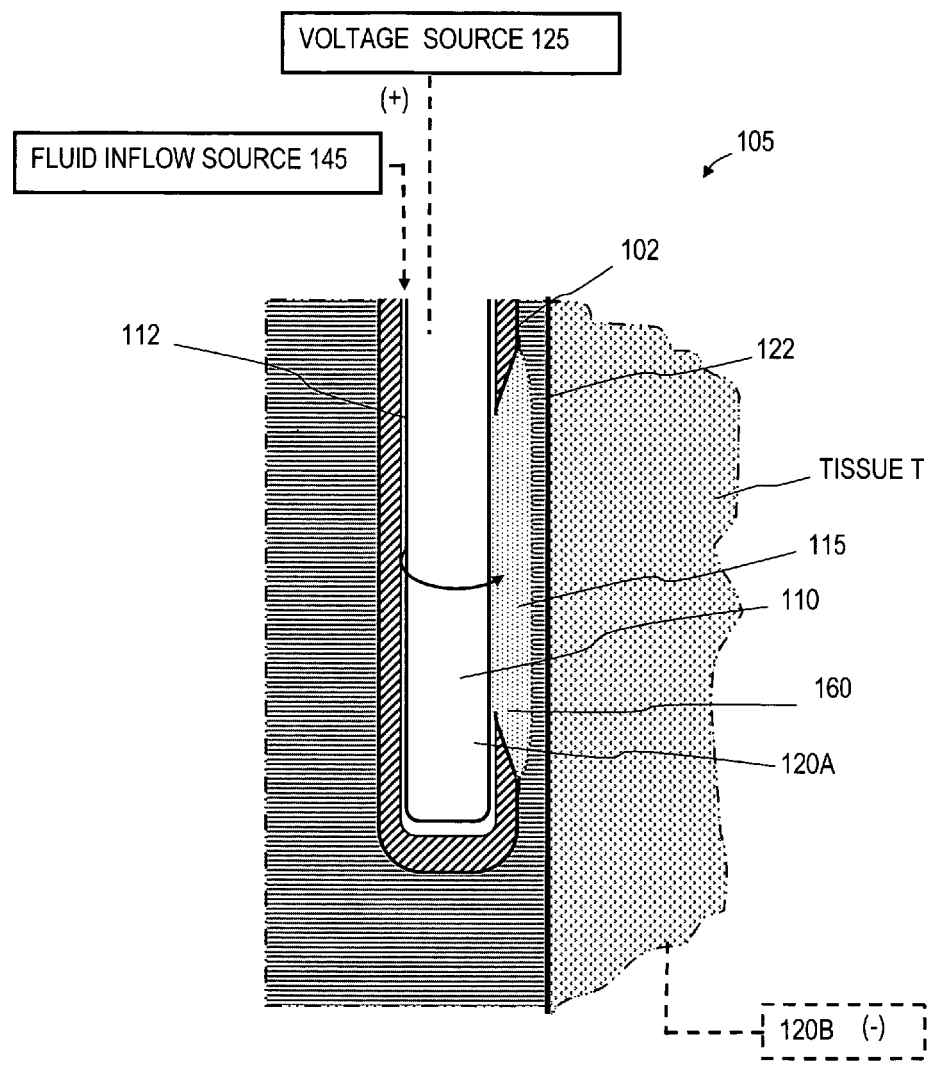
FIG. 5 is a cut-away view of another embodiment of working end with an actuatable member for creating supercavitation in a side port or recess in a sleeve member.

In another working end embodiment 105 depicted in FIG. 5, a rotatable member 110 has an exposed working surface 114 in a window or port 160 in an elongated shaft member 102. An embodiment in the configuration of FIG. 5 can be used to create a localized supercavity 115 in a selected angular region for ablating a side of a body lumen such as in a TURP procedure or in the ablation of endoluminal occlusive material. The first polarity electrode 120A can be a portion of rotatable element 110 as depicted in FIG. 5. In this embodiment, the second opposing polarity electrode can be spaced apart on an opposing portion of rotatable member 110 or on the shaft member 102, or a combination thereof. In another similar embodiment, a working end 105 as in FIG. 5 can be carried at the distal end of an elongated flexible catheter configured for endoluminal navigation. The cavitation inducing surface 114 also can be flexible member, for example as used in a cutting loop used in a TURP procedure.

Figure 6:
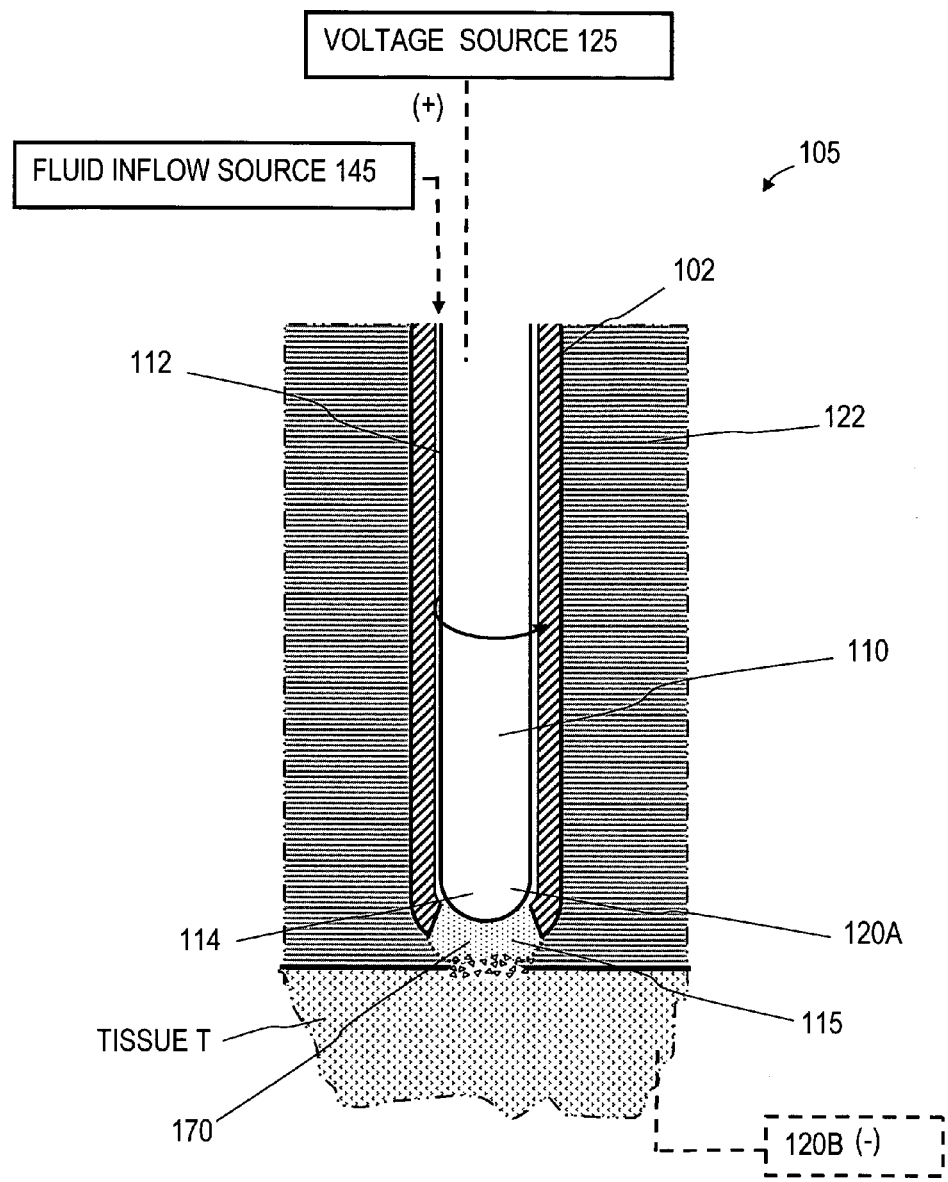
FIG. 6 is a cut-away view of another embodiment of working end with an actuatable member for creating supercavitation in a distal recessed portion of an elongate shaft.

In another embodiment, the apparatus of the invention comprise a working end 105 that carries an elongated actuatable member 110 (similar to FIG. 6) coupled to an ultrasound source, such as one or more piezoelectric elements. The ultrasound source is configured for oscillating the working surface 114 at a rate capable of localized lowering of the pressure of a surrounding liquid substance to below its saturated vapor pressure to create a cavity therein. In one embodiment, the working surface is actuatable in rotation as described above and is also actuatable by ultrasound to achieve surface speeds of 70 m/sec or more to thereby lower the pressure of liquid substance to below its saturated vapor pressure to thereby create a cavity therein. In these embodiments, the method of the invention again contemporaneously delivers electrical energy across the supercavity to body structure adjacent the working end As shown, the working end 105 includes with an actuatable member 110 for creating supercavitation in a distal recessed portion 170 of an elongate shaft 102.

Figure 7:
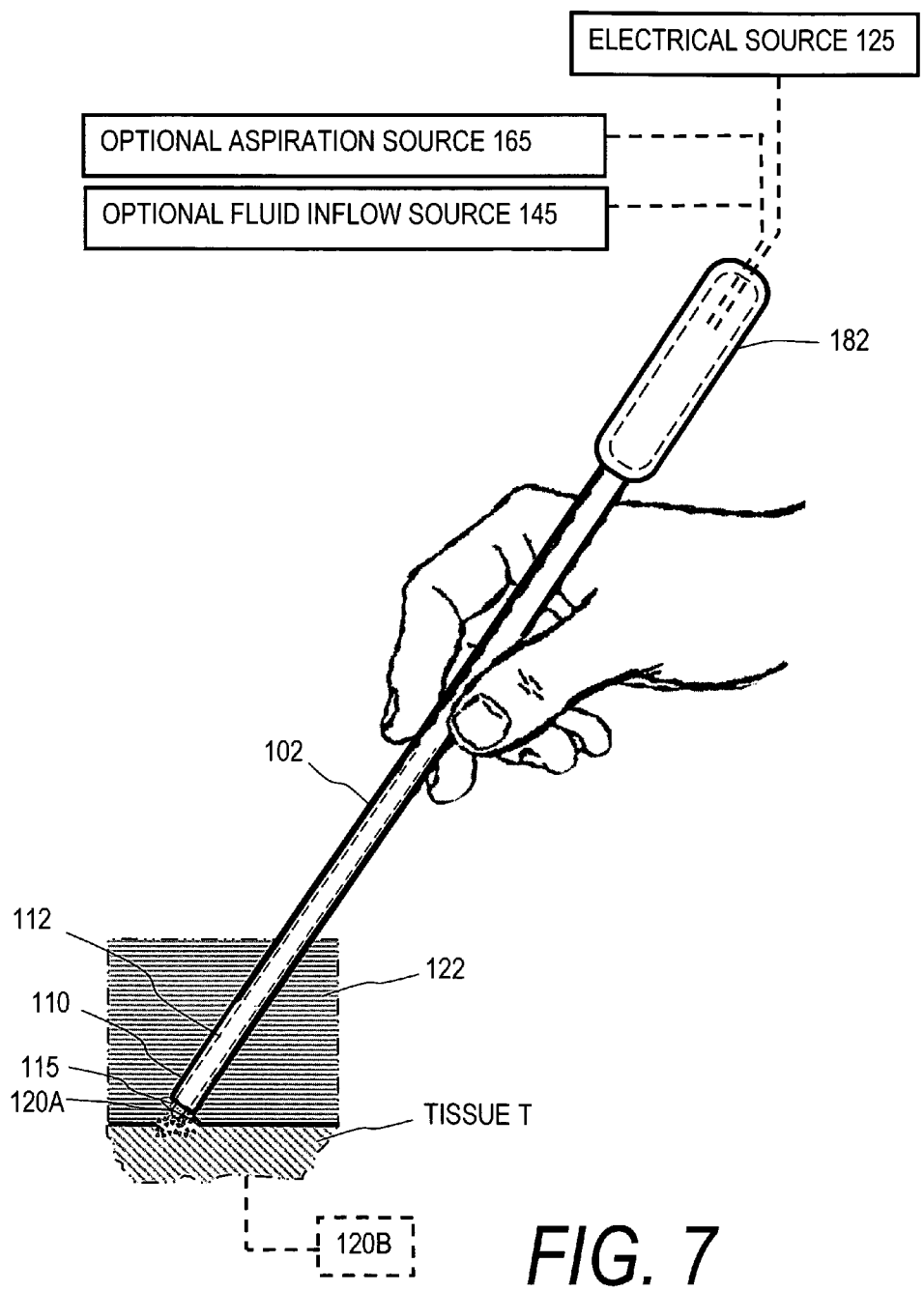
FIG. 7 is a cut-away view of another embodiment of working end with an actuatable member for creating supercavitation wherein the working end includes an aspiration source coupled to a flow channel in the working end.

In another embodiment depicted in FIG. 7, the apparatus of the invention further includes an aspiration source 165 for aspirating fluid and ablation debris from the targeted site. The aspiration source is coupled to an open-ended channel 138 extend through the center of a tubular rotating member 110 as in FIG. 2D, or the aspiration means can be coupled to bore 112 in which the member 110 rotates (see FIG. 1). In another embodiment, the working end includes a cavitation-inducing surface 114 that is adjustable in extension from the distal end of shaft member 102 to provide different cavity dimensions.

In one embodiment of the invention depicted in FIG. 7, the system is configured with a de-mateable, disposable shaft 102 and working end 105 that is coupled handle portion 182 that carries the motor drive. Such a device can be dimensioned for use in arthroscopic procedures to treat and ablate a targeted site within a joint.

In any embodiment, the system includes a computer controller operatively connected to the high frequency electrical energy source 125 to control delivery of electrical delivery. In one embodiment, the system and controller include an electrode arrangement for sensing impedance across a supercavity 115 as in FIG. 1 to initiate, modulate or terminate energy delivery. The controller also can modulate energy delivery upon sensing a selected rate of rotation or oscillation. The controller also can modulate a pulsed energy delivery repetition rate. Alternatively, any sort of on-off switch in a foot pedal or hand switch can be used to actuate the voltage source and controller 125 when using operating the system.

The cavitation-enabled electrosurgical surfaces and methods above have been described in connection with several surgical procedures for volumetric tissue removal, such as in ablating a hole in scleral tissue to treat glaucoma (FIG. 4) and in tissue ablation in TURP procedures. It will be clear to those having skill in the art that the system has operational characteristics that may be suitable for a wide range of volumetric tissue removal procedures in, or on, structure of a mammalian body. For example, the system has other uses in ophthalmology such as in cutting retinal tissue, cutting a lens capsule in capsularhexis procedures, or fracturing and aspirating a lens nucleus in a cataract procedure. The system and method of the invention are suitable for arthroscopic surgeries, including partial meniscectomies, synovectonies, chondroplasties, tendon and cartilage removals, and in general resurfacing and texturing of cartilage, tendon and bone surfaces. In addition, in the ENT and GI fields, there are a variety of procedures that require volumetric tissue removal either at a tissue surface or at the end of a probe inserted percutaneously in treating nose and throat disorders, for example, soft palate volume reduction surgery, turbinate reduction surgery, sinus surgery and jaw bone surgery. The system can be used in skin resurfacing with a thin layer of fluid or gel placed over the skin. The system also can be used in spine surgery and neurosurgery in which collateral thermal damage can be prevented. These procedures require that the surgeon be provided with means to remove tissue in close proximity to delicate structures and nerves that cannot be damaged, which procedures lend themselves to the methods disclosed herein.

In many surgical fields, the selective removal of malignant tissue or other tumors may be accomplished by the present invention, such as in breast tumors or liver tumors. For example, a form of stereotactic-directed probe may be used to ablate breast lesions. The use of the system in tumor ablation and removal is assisted by the fact that a supercavitation is viewable under ultrasound imaging for controlling margins of ablation.

The method of the invention also may have use in interventional cardiology to remove vascular occlusions or in CTO procedures to ablate a hole in a calcified cap of a chronic total occlusion. The method of the invention also may be useful for drilling holes in tissue such as in TMR procedures (transmyocardial revascularization). The material removal methods described above apply to all body structures, which include accretions, calculi and the like.

Those skilled in the art will appreciate that the exemplary embodiments and descriptions thereof are merely illustrative of the invention as a whole, and that variations in controlling the duration of intervals of energy delivery, in controlling the repetition rate, and in controlling the voltage applied to create the interval of intense electric fields may be made within the spirit and scope of the invention. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. Particular features that are presented in dependent claims can be combined and fall within the scope of the invention. The invention also encompasses embodiments as if dependent claims were alternatively written in a multiple dependent claim format with reference to other independent claims.

What is claimed is:

1. An electrosurgical method for applying electrical energy to body structure comprising:
    (a) immersing an electrosurgical surface in a liquid substance,
    (b) providing a rate of motion in the electrosurgical surface capable of localized lowering of the pressure of the substance below the saturated vapor pressure thereof to create a cavity; and
    (c) applying the electrical energy from the electrosurgical surface across the cavity in close proximity to mammalian body structure thereby applying the electrical energy to the body structure.

2. The electrosurgical method of claim 1 including providing the rate of motion of at least 70 m/sec.

3. The electrosurgical method of claim 1 including providing the rate of motion by at least one of rotation of the electrosurgical surface and ultrasonic actuation of the electrosurgical surface.

4. The electrosurgical method of claim 1 wherein step (c) ablates a portion of the body structure.

5. The electrosurgical method of claim 4 further comprising translating the electrosurgical surface to apply the electrical energy to a surface portion of the body structure.

6. The electrosurgical method of claim 4 further comprising penetrating the electrosurgical surface into a tissue of the mammalian body structure to ablate a path in the tissue.

7. The electrosurgical method of claim 1 wherein the applying of the electrical energy across the cavity is carried out between first and second opposing polarity portions of the electrosurgical surface.

8. The electrosurgical method of claim 1 wherein the applying of the electrical energy across the cavity is carried out between a first polarity of the electrosurgical surface and a second polarity of a ground pad.

9. An electrosurgical method for applying electrical energy to body structure comprising:
    (a) immersing a working end including a moveable working surface in a liquid substance,
    (b) providing a rate of motion in the working surface capable of localized lowering of the pressure of the substance below the saturated vapor pressure thereof to create a cavity; and
    (c) applying the electrical energy across the cavity in close proximity to mammalian body structure thereby applying the electrical energy to said body structure.

10. The electrosurgical method of claim 9 wherein providing the rate of motion in the working surface causes localized increase of the impedance of the substance by a factor of at least one hundred.

11. The electrosurgical method of claim 9 wherein providing the rate of motion in the working surface causes localized increase of the impedance of the substance by a factor of at least one thousand.

12. The electrosurgical method of claim 9 wherein the applying of the electrical energy across the cavity is carried by at least one electrode in the working end.

13. The electrosurgical method of claim 9 wherein the applying of the electrical energy across the cavity is carried by at least one electrode in the working surface.

* * * * *